United States Patent [19]
Hogg

[11] 4,077,749
[45] Mar. 7, 1978

[54] SAMPLE EJECTION SYSTEM INCLUDING TEMPERATURE CONTROL

[75] Inventor: Walter R. Hogg, Miami Lakes, Fla.

[73] Assignee: Coulter Electronics, Inc., Hialeah, Fla.

[21] Appl. No.: 643,920

[22] Filed: Dec. 23, 1975

Related U.S. Application Data

[63] Continuation-in-part of Ser. No. 493,828, Aug. 1, 1974, Pat. No. 3,939,409.

[51] Int. Cl.² .............. G01N 27/00; F04B 35/00
[52] U.S. Cl. .............................. 417/321; 324/71 CP
[58] Field of Search .............. 417/52, 207, 410, 379; 324/71 CP

[56] References Cited
U.S. PATENT DOCUMENTS

| | | | |
|---|---|---|---|
| 3,859,012 | 1/1975 | Hogg | 417/437 |
| 3,936,741 | 2/1976 | Coulter et al. | 324/71 CP |
| 3,961,249 | 6/1976 | Coulter | 324/71 CP |
| 3,973,196 | 8/1976 | Hogg | 324/71 CP |

*Primary Examiner*—William L. Freeh
*Attorney, Agent, or Firm*—Silverman & Cass, Ltd.

[57] ABSTRACT

A sample ejection system includes a sample ejecting device which receives and temporarily stores an aliquot of sample. A thermal expansion device in the sample ejecting device operates upon application of energy to expand and eject a predetermined volume of sample. Thermal conduction structure coupled to the sample ejecting device operates in a first mode to cool and contract the expansion device.

24 Claims, 5 Drawing Figures

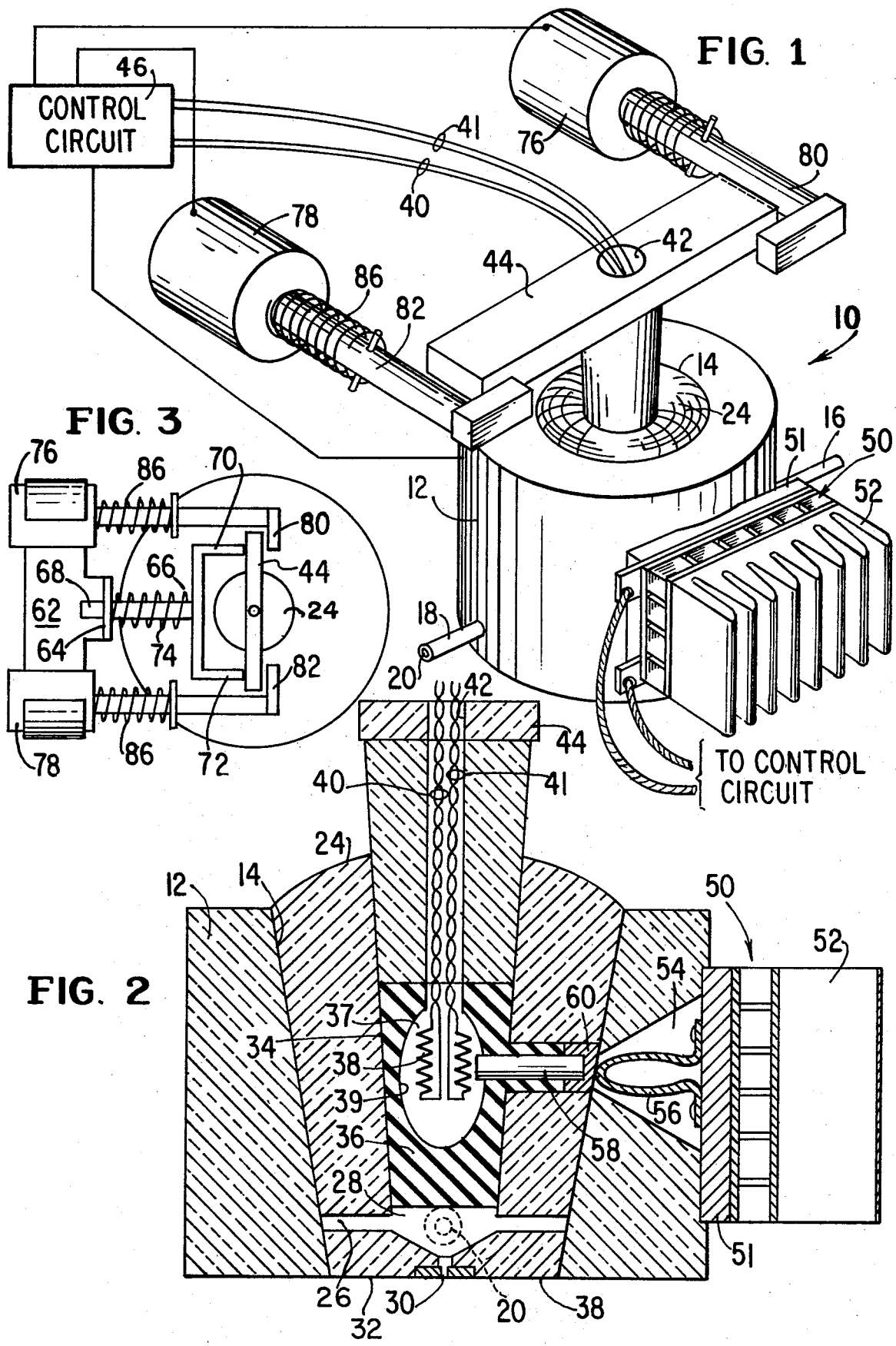

SAMPLE EJECTION SYSTEM INCLUDING TEMPERATURE CONTROL

CROSS-REFERENCE TO RELATED APPLICATIONS

This application is a Continuation-in-Part of U.S. patent application Ser. No. 493,828 filed Aug. 1, 1974 now U.S. Pat. No. 3,939,409.

This application is related to the U.S. Pat. Nos. 3,859,012 and 3,890,569 and to U.S. patent application Ser. No. 584,142 filed June 5, 1975 now U.S. Pat. No. 3,973,196. The noted patents and patent application are to be considered incorporated by reference herein to the extent required.

All of the above noted patents and patent applications are owned by the same Assignee as this application.

BACKGROUND OF THE INVENTION

The invention relates to a non-diluting particle study device and more specifically to a device for ejecting a non-diluted specific minute amount of fluid sample containing particles into a flow stream leading to a sensing zone in a particle study device.

Heretofore, in the field of particle analysis and particle study, such as the study of red and white blood cells in a blood sample, it has been common practice to dilute the blood sample and then to pass a portion of the diluted sample through a sensing zone in a particle study device. The blood is diluted because the normal human blood count is five million cells per cubic millimeter and it is only necessary to study or analyze one hundredth of that amount, namely, a volume of 0.01 cubic millimeters.

In studying a blood sample, the blood cells in a given amount of the sample are counted by passing a portion of the diluted blood sample through a sensing zone in a particle analyzing device, such as a particle analyzing device which operates on the sensing principle disclosed in U.S. Pat. No. 2,656,508 issued Oct. 20, 1953 to Wallace H. Coulter.

According to this principle, when a microscopic particle in suspension in a fluid electrolyte is passed through an electrical field of small dimensions approaching those of the particle, there will be a momentary change in the electric impedance of the electrolyte in the ambit of the field. This change of impedance diverts some of the excitation energy into associated electrical circuitry, giving rise to an electrical signal. Such signal has been accepted as a reasonably accurate indication of the particle volume for most biological and industrial purposes.

One apparatus of the above type includes first and second vessels each containing a body of fluid electrolyte. The second vessel is smaller and is immersed in the electrolyte in the first vessel. An electrode extends into the electrolyte in each vessel and electric current flows between the electrode through an opening in the side wall of the second vessel, the opening consisting of a minute aperture. Flow of liquid between the vessels is caused by applying vacuum to the second vessel. Particles passing through the aperture from one body of electrolyte to the other body of electrolyte will change the impedance of the electrolyte contained within the aperture and this change in impedance is sensed by the electrodes. This change generates an electrical signal in the form of a particle pulse which is then counted by the electrical circuitry of the particle analyzing device.

When making a blood analysis a dilution of blood in electrolyte is placed in the first vessel. Then vacuum is applied to the second vessel to cause diluted blood to flow from the first vessel through the aperture into the second vessel for a specific period of time, usually the time required to pass a known aliquot of suspension. The second vessel is filled with electrolyte, probably including prior dilutions.

To make a fairly accurate measurement of particle concentration, one must accurately measure or meter the amount of fluid which passes through the sensing zone during a period of time when the electrical circuitry of the device is operative. This can be accomplished by passing fluid through the sensing zone at a given flow rate for a specified period of time. Apparatus utilizing fluid flow metering systems of this type is a fluid analyzing device are disclosed in U.S. Pats. Nos. 3,577,162 and 3,654,439.

In most particle analyzing devices of the type noted, the metering is accomplished with a fluid metering apparatus of the type disclosed in U.S. Pats. Nos. 2,869,078, 3,015,775 and 3,271,627. Such metering apparatus includes a closed fluid system hydraulically connected to the second vessel. The closed fluid system includes a connection to a vacuum source and a mercury manometer. When operating the device, vacuum is applied to the closed fluid system to raise the mercury in the manometer and to draw some fluid sample into the second vessel. The connection to the vacuum source is then closed and the manometer, by reason of the mercury flowing downwardly to its original position, causes liquid to be drawn through the aperture and generates signals indicating the beginning and the end of an analytic run in a period during which an accurately metered volume of fluid is passed through the aperture. The metered volume of fluid is equal to the volume within the manometer between two electrodes.

It will be understood from the foregoing description of a particle analyzing device that it is necessary to dilute a quantity of blood, to make an accurate determination of dilution and to accurately meter the fluid flow through the minute aperture in order that an accurate count of blood cells can be made. A simpler way of making the particle analysis or study would be to pass a specific minute amount of undiluted blood through the minute aperture and thereby eliminate the manometer and diluter systems. A device for ejecting a specific minute amount of particle-containing fluid such as blood into the flow stream leading to a sensing zone in a particle analyzing device is shown in U.S. Pat. Nos. 3,859,012 and 3,890,569.

The ejecting devices described in both above noted patents may be incorporated into automated systems wherein a sample such as blood is passed to the device on a continuous basis. One such system is shown in the Parent patent application Ser. No. 493,828 filed Aug. 1, 1974 now U.S. Pat. No. 3,939,409. In this system the ejecting device is mounted in a stopcock assembly and the sample is supplied continuously with an aliquot being trapped in a compartment prior to operation of the ejection device.

In the above noted U.S. Pat. Nos. 3,859,012 and 3,890,569 circuitry is disclosed for operating the ejecting device. The circuitry provides a predetermined amount of electrical energy to the device causing it to increase in temperature, expand and eject a specific amount of fluid. The amount of energy provided is determined mathematically and, in the embodiment described therein, is the amount of energy necessary to raise the temperature of the device twenty degrees, a twenty degree rise causing a specific expansion and therefore an ejection of a specific amount of fluid.

In U.S. patent application Ser. No. 584,142 filed June 5, 1975, now U.S. Pat. No. 3,973,196 circuitry also is disclosed for operating the ejecting device. This circuitry operates to raise the temperature of the device by a specific amount in excess of the device temperature at the start of the expansion process, and supplies whatever energy is necessary to raise the temperature the desired amount.

In the ejecting devices noted if sufficient thermal insulation is used to ensure that heat loss during a heating cycle is not excessive, an extended cool-off period is necessary. Extended cool-off periods are undesirable from an operational point of view, particularly in an automated system. In systems where operating speed is important such as automated systems, it is desirable to have some means for providing a rapid cooling of the ejecting device.

SUMMARY OF THE INVENTION

In practicing this invention, a sample ejecting system is provided which includes a sample ejecting device having structure for receiving and temporarily storing an aliquot of sample. The sample ejecting device includes a thermal expansion device mounted within the receiving and storing structure which operates upon application of energy to heat and expand for ejecting a predetermined volume of sample. A thermal conduction structure is a part of the ejecting system and is coupled to the sample ejecting device. The thermal conduction structure is operative after expansion of the thermal expansion device to conduct heat from the sample ejecting device for cooling and contracting the thermal expansion device.

BRIEF DESCRIPTION OF THE DRAWINGS

FIG. 1 is a combined perspective view and block diagram of the sample ejecting system.

FIG. 2 is a section view of the sample ejecting device which includes the features of this invention;

FIG. 3 is a plan view of the sample ejecting device and a portion of the control circuit.

Figure 4:
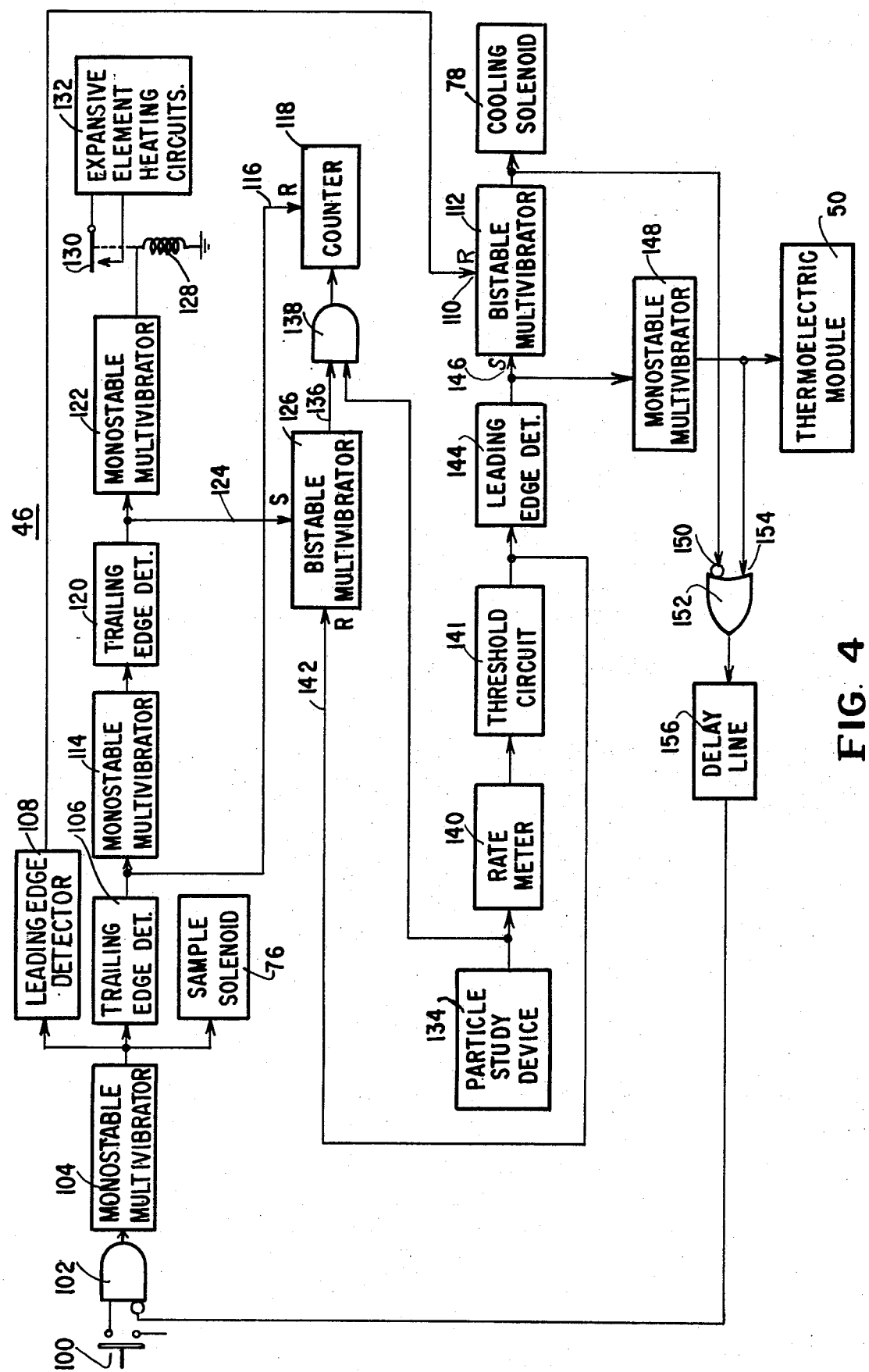
FIG. 4 is a block diagram of the control circuit used in the system shown in FIG. 1.

DESCRIPTION OF THE PREFERRED EMBODIMENT:

Referring to FIGS. 1 and 2, the specific embodiment of the sample ejecting device shown is a stopcock assembly similar to that employed in the Parent application. Stopcock assembly 10 includes a housing 12 formed from glass or other insulating material. The housing includes a truncated cone shaped chamber 14. Pipes 16 and 18 are formed into housing 12 and include a conduit 20 passing therethrough and connecting with the chamber 14. These pipes constitute input and output ports respectively.

A stopcock valve 24 is fitted into chamber 14 and rotates therein. Stopcock valve 24 has a conduit 26 passing therethrough which connects with conduit 20 when stopcock valve 24 is rotated to a first position. Conduit 26 connects with sample accumulation chamber 28 formed substantially in the center of stopcock valve 24. A minute opening 30 is formed in sidewall 32 of stopcock valve 24 and connects with chamber 28 thereby providing three separate openings to chamber 28 in stopcock valve 24.

Positioned in chamber 28 of stopcock valve 24 is an expansive element 34 such as is shown and described in U.S. Pat. Nos. 3,859,012; 3,890,569 and in the Parent and incorporated applications. Expansive element 34 includes an elastic outer member 36 surrounding a thermal expansion element 37. A resistor 38 and a thermistor 39 are embedded in the thermal expansion element 37. A pair of wires 40 secured to the terminals of resistor 38, and a pair of wires 41 secured to the terminals of thermistor 39 pass through thermal expansion element 37 and elastic outer member 36 and extend through an aperture 42 formed in handle 44. Wires 40 and 41 are connected to a control circuit 46.

In the embodiment shown, a thermoelectric module 50, oftentimes referred to as a "Peltier junction" is shown secured to a heavy metal plate 51 which is secured to the outer wall of housing 12. Secured to thermoelectric module 50 is a heat dissipation structure 52 which takes the form of a number of metallic fins secured to a metallic base. Heat dissipation structure 52 is more commonly referred to as a heat sink. It may or may not have cooling fins as shown. Thermoelectric module 50 is electrically actuated by control circuit 46 and develops a cold surface by use of a thermoelectric process. Plate 51 evenly conducts heat coupled thereto to the entire cold surface. Heat is also generated during the process and the heat is dissipated by heat sink 52.

One or more openings 54 are formed at specific locations in housing 12 and extend from the outer surface of housing 12 to the surface defining chamber 14. In FIG. 2 only a single opening is shown. A spring finger 56 is seated in each such opening 54 and is secured at its one end to plate 51. Each finger extends through opening 54 and slightly into housing chamber 14 and is formed from a suitable highly thermally conductive material such as, for example, beryllium copper.

One or more heat conductors 58 extend radially in stopcock valve 24. Each heat conductor 58 passes into thermal expansion element 37 and extends through elastic outer member 36 of expansive element 34 terminating at a plug 60 which extends to the edge of stopcock valve 24 that seats in housing chamber 14. Heat conductor 58 and plug 60 are formed from a highly thermally conductive material which may be metallic or may be a non-metallic highly conductive material such as, for example, beryllium oxide. It must be chosen to resist wear due to friction against thermal contact finger 56.

In operation, handle 44 of stopcock valve 24 is rotated to a first position, either manually or via an automatic control mechanism. In the first position, conduit 20 is connected directly to conduit 26 and chamber 28 allowing a fluid sample such as blood to be entered into chamber 28. The sample is forced into chamber 28 by a suction drawing on conduit 20 or by a pressure forcing the fluid into conduit 20 and chamber 28. When the sample has been entered into chamber 28, handle 44 is rotated to a second, center position turning stopcock valve 24 and breaking the connection between conduit 26 and conduit 20. In this second position, an aliquot of sample is trapped in chamber 28. Energy is applied to expansive element 34 while stopcock valve 24 is in this second position in order to heat and expand element 34 and eject a predetermined quantity of sample through aperture 30. When expansive element 34 has expanded completely so that the desired amount of sample has been ejected through opening 30, handle 44 is rotated to a third position. In this third position each heat conductor 58 and plug 60 is rotated into contact with a spring finger 56 thus providing a highly thermally conductive path between the heated thermal expansion element 37 and the plate 51, thermoelectric module 50 and heat sink 52. This connection and the actuation of thermoelectric module 50 results in a rapid dissipation of the heat developed in thermal expansion element 37, and thus a rapid contraction of expansion element 37 back to its original or normal size. When the cooling process is completed, and it is desired to again initiate another operating cycle, handle 44 is rotated back to the first position.

Referring now to FIG. 3, one mechanism for rotating handle 44 of stopcock valve 24 is shown in greater detail. A pivot mechanism 62 is shown positioned adjacent handle 44 and includes a mounting plate 64 which may be secured to a wall or to the same structure which holds and supports stopcock assembly 10. A fork shaped structure 66 includes a handle portion 68 and two finger portions 70 and 72 which extend toward the opposite ends of handle 44 from an end of handle portion 68. A spring 74 extends between mounting plate 64 and the end of handle portion 68 to which fingers 70 and 72 are attached. The spring exerts a pressure against fork shaped member 66 and mounting plate 64 causing fingers 70 and 72 to bear against handle 44. This pressure causes handle 44 to be held in its second or center position.

Solenoids 76 and 78 are positioned adjacent to the mechanism 62 and also are mounted thereto. These solenoids are considered to be a part of control circuit 46 as will be explained in greater detail subsequently in this application. Control fingers 80 and 82 are seated in solenoids 76 and 78 respectively and extend to a point adjacent the opposite ends of handle 44. When solenoid 76 is operated it will draw control finger 80 into solenoid 76. As control finger 80 is drawn into solenoid 76 the end adjacent handle 44 will contact handle 44 causing handle 44 to rotate in a counter-clockwise direction. When control finger 80 completes its travel into solenoid 76, handle 44 will be rotated in a counter-clockwise direction to its first position whereby conduit 20 in pipes 16 and 18 is connected to conduit 26. Upon deactivation of solenoid 76, control finger 80 will return to its normal or extended position by action of spring 84, and handle 44 will return to its second or center position by action of the pivot mechanism 62.

Solenoid 78 operates in a manner similar to solenoid 76 and when actuated will draw control finger 82 into the solenoid 78. As control finger 82 is drawn into solenoid 78, the end adjacent handle 44 will contact handle 44 causing the handle to rotate in a clockwise direction. When control finger 82 is drawn into solenoid 78 the maximum distance, handle 44 will be rotated to its third position. Upon deactivation of solenoid 78, control finger 82 will return to its outermost position by the spring action of spring 86 and handle 44 will return to its second position by operation of pivot mechanism 62.

Figure 5:
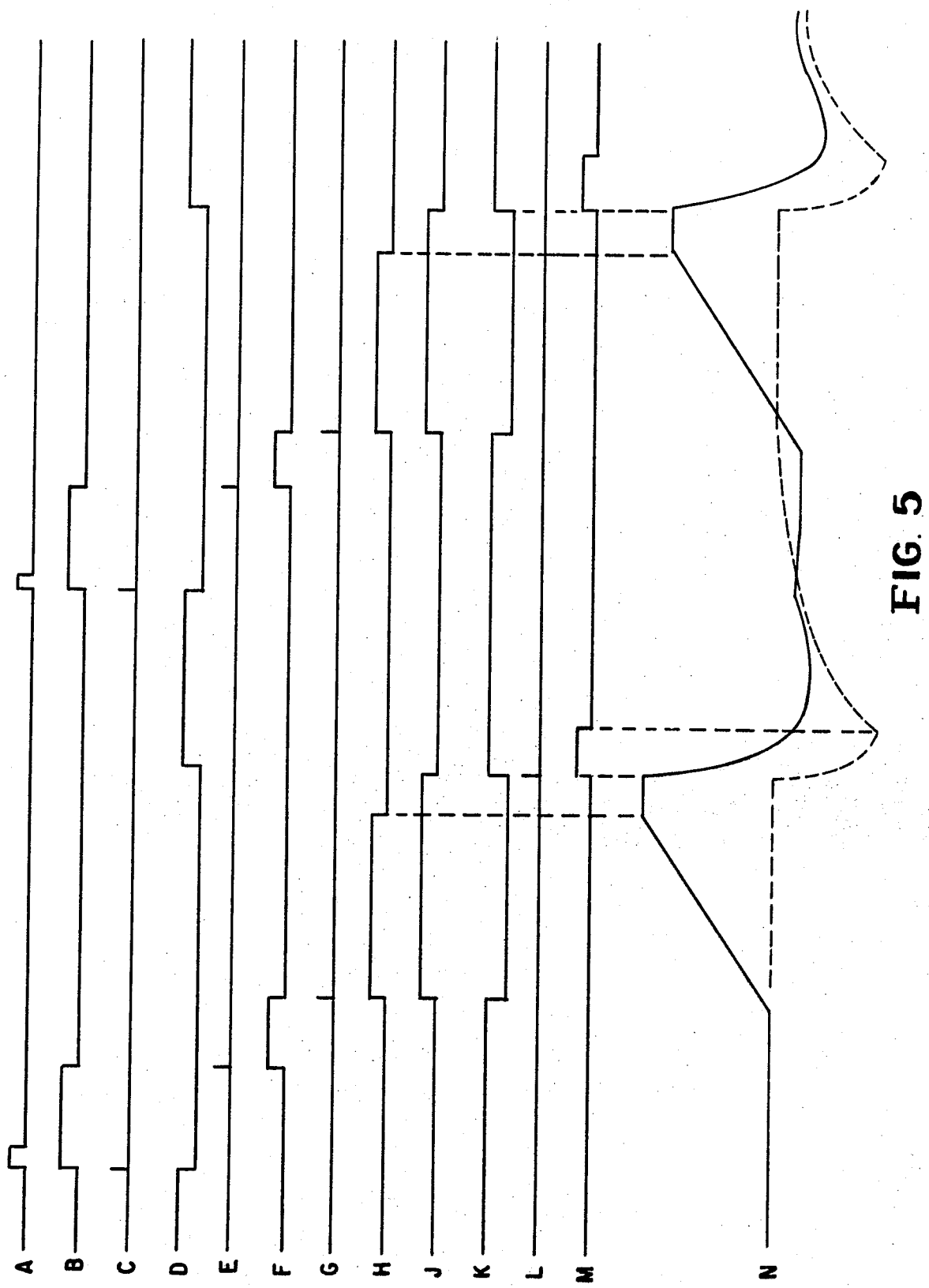
FIG. 5 is a waveform diagram of signals at various points in the block diagram of FIG. 3.

Referring now to FIGS. 4 and 5, the block diagram and timing waveform diagrams for control circuit 46 are shown. In order to initiate system operation, start switch 100 is actuated coupling a start pulse, shown in waveform A of FIG. 5, to one input of AND gate 102. The second input of AND gate 102 is an inverted input, and for the purpose of explaining this operation assume that the input signal at the second input is a low state or zero level signal so that with the receipt of the start pulse from start switch 100 AND gate 102 will develop a high state signal which is coupled to a monostable multivibrator 104. Monostable multivibrator 104, commonly known as a one-shot, will develop a high state or one level signal, shown in waveform B of FIG. 5, in response to the signal received from AND gate 102. The high state signal developed by monostable multivibrator 104 is coupled to sample solenoid 76, a trailing edge detector (T.E.D.) 106 and leading edge detector (L.E.D.) 108.

Sample solenoid 76 actuates in response to the signal from monostable multivibrator 104 causing arm 80, shown in FIG. 3, to be drawn into the solenoid and handle 44 to be rotated to the first position. During the interval that monostable multivibrator 104 develops this high state signal, and while stopcock valve 24 is in the first position, the fluid sample path is completed and fluid sample is passed through conduit 20 and pipes 16 and 18 into conduit 26 and chamber 28 in stopcock assembly 10. When the high state signal developed by monostable multivibrator 104 terminates sample solenoid 76 is deactivated and handle 44 returns to its second position.

Leading edge detector 108 develops a pulse shown in waveform C of FIG. 5, in response to the leading edge of the high state signal developed by monostable multivibrator 104. The pulse developed by leading edge detector 108 is coupled to the reset input 110 of a bistable multivibrator 112 causing bistable multivibrator 112 to return or reset as shown in waveform D of FIG. 5. This allows deactivation of solenoid 78. It is to be understood that deactivation of solenoid 78 and activation of solenoid 76 occur substantially simultaneously.

The trailing edge of the high state signal developed by monostable multivibrator 104 is detected by trailing edge detector 106 which develops a pulse in response thereto shown in waveform E of FIG. 5. The pulse developed by trailing edge detector 106 is coupled to a monostable multivibrator 114 and to the reset input 116 of a counter 118. The pulse coupled to reset input of counter 118 causes the counter to reset to a zero count. The pulse coupled to monostable multivibrator 114 causes it to change states and develop a high level signal shown in waveform F of FIG. 5. Monostable multivibrator 114 is employed simply to provide a fixed amount of operational delay to insure that any undesired transients have subsided. The high state signal developed by monostable multivibrator 114 is coupled to a trailing edge detector 120 which develops a pulse shown in waveform G of FIG. 5 in response to the trailing edge of the high state signal developed by monostable multivibrator 114.

The pulse developed by trailing edge detector 120 is coupled to monostable multivibrator 122 and to the "set" input 124 of a bistable multivibrator 126, more commonly known as a flip-flop. Monostable multivibrator 122 will develop a high state signal in response to the pulse from trailing edge detector 120 which is shown in waveform H of FIG. 5. This high state signal is coupled to the coil of a relay 128 causing contacts 130 to close. Contacts 130 form the start contacts for the expansive element heating circuit 132. Expansive element heating circuit 132 can be a circuit such as is shown in U.S. Pat. No. 3,859,012, or, if the thermistor 39 shown in FIG. 2 is employed, then the circuitry such shown and described in U.S. patent application Ser. No.

584,142 now U.S. Pat. No. 3,973,196 may be employed. In this latter circuitry, relay contacts 130 replace the start switch shown in the patent application.

During the time the monostable multivibrator 122 develops a high state signal, expansive element heating circuit 132 supplies energy to and heats the thermal expansion element 37 in expansive element 34 in stopcock assembly 10. The temperature of expansion element 37 is shown in waveform N by a solid line and causes expansive element 34 to expand, as more completely described in the incorporated patents, and eject a specific predetermined amount of fluid sample through the minute aperture 30 shown in FIG. 1.

Assuming that the sample is blood, and further assuming the stopcock assembly 10 is attached to a particle study device, represented in FIG. 4 by a block 134, such as is shown in greater detail in the Parent U.S. application, the blood cells in the sample will be detected as they pass through a microscopic aperture in the particle study device 134. Particle study device 134 will develop a particle pulse in response to each detected particle. While the sample is being ejected from chamber 28 and for some short period thereafter, a substantial number of particles will pass through particle study device 134 and will be detected. Before and after ejection of the sample from chamber 28 very few particles will pass through particle study device 134 and be detected.

As noted previously, the pulse developed by trailing edge detector 120, shown by waveform G in FIG. 5, is coupled to "set" input 124 of bistable multivibrator 126. This pulse will cause bistable multivibrator 126 to change states and develop a high state signal which is coupled by conductor 136 to one input of AND gate 138. This high state signal is shown in waveform J of FIG. 5. With a high state signal at the one input of AND gate 138, each high state signal developed at the second input of AND gate 138 will cause the output of the AND gate 138 to change to a high state signal. Each high state signal developed at the output of AND gate 138 will actuate counter 118 to increase its count by one. AND gate 138 is receiving a high state signal at conductor 136 while expansive element 34 is receiving energy from heating circuit 132. Consequently, the particles being expelled from chamber 28 and passed to particle study device 134 will cause particle study device 134 to develop particle pulses, and each particle pulse develops a high state signal that is coupled from particle study device 134 to the second input of AND gate 138 causing the counter to count each detected particle pulse.

The particle pulses developed by particle study device 134 are also coupled to a ratemeter 140. Ratemeter 140 develops a DC voltage which is proportional in amplitude to the repetition rate of pulses received by ratemeter 140. The voltage developed by ratemeter 140 is coupled to a threshold circuit 141. When the particle pulses developed occur at less than a particular repetition rate, thus indicating that all of the blood cells in the sample ejected from chamber 28 have passed through particle study device 134, the signal developed by ratemeter 140 will fall below a threshold level causing threshold circuit 141 to develop the upper level threshold signal shown in waveform K of FIG. 5, which is coupled to the reset input 142 of bistable multivibrator 126 and to a leading edge detector 144. The threshold signal coupled to the reset input 142 of bistable multivibrator 126 will reset multivibrator 126 as shown in waveform J thus inhibiting AND gate 138 and further inhibiting any additional count by counter 118.

The threshold signal coupled to leading edge detector 144 will cause detector 144 to develop a pulse, shown in waveform L of FIG. 5, which is coupled to the "set" input 146 of bistable multivibrator 112 and to a monostable multivibrator 148. Bistable multivibrator 112 is in a reset state at the time of receipt of the pulse at set input 146 so that bistable multivibrator will change states in response to this pulse and develop a high state signal. The high state signal is coupled to cooling solenoid 78 and to an inverted input 150 of OR gate 152.

The high state signal developed by bistable multivibrator 112 will cause solenoid 78 to actuate thus rotating handle 44 and stopcock valve 24 to the third position wherein heat conductor 58 and fingers 56 shown in FIG. 2 are connected. The pulse of leading edge detector 144 coupled to monostable 148 causes monostable 148 to change states and develop a high state signal shown in waveform M which is coupled to thermoelectric module 50 and to the second input 154 of OR gate 150.

Thermoelectric module 50 operates in response to the monostable signal to begin cooling and the temperature of its cold surface is represented by the dashed line waveform in waveform N of FIG. 5. The rapid cooling produced by thermoelectric module 50 and the conduction of heat generated by the module 50 away from the assembly by way of heat sink 52 causes a rapid cooling of expansive element 34. The time period during which monostable multivibrator 148 develops a high state signal is selected so that thermoelectric module 50 operates for a period of time sufficient for the expansive element 34 to cool once again to approximately ambient temperature as shown by the solid waveform N of FIG. 5. Hence, its volume returns approximately to its normal value. If it is not returned exactly to its original temperature, the thermistor 39 and associated circuitry will compensate as described in U.S. patent application Ser. No. 584,142 now U.S. Pat. No. 3,973,196.

At the termination of the high state signal developed by monostable multivibrator 148 the output of OR gate 152 will change from a high state to a low state signal. This low state signal is coupled through delay line 156 where it is delayed slightly. Delay line 156 is employed in order to prevent the inhibiting of the start function upon operation of start switch 100 by the possible instantaneous response of the entire control circuit. The output of delay line 156 is coupled to the second or inverted input of AND gate 102. With a low state or zero level signal coupled to this inverted input AND gate 102 will once again be able to develop a high state signal at its output in response to actuation of start switch 100.

Upon initiation of the next operating cycle by actuation of switch 100 the operating cycle described previously will be repeated. It should be noted however that until the second operating cycle is repeated, stopcock valve 24 is maintained in its third position by cooling solenoid 78. When bistable multivibrator 112 is reset, after the initiation of a new operating cycle, cooling solenoid 78 is deactivated as shown in waveform D, returning stopcock valve 24 to its second position and simultaneously solenoid 76 moves the valve to its first position.

Although a single embodiment has been shown and described, it is to be understood that modifications and variations to the system heretofore described are within the scope of the invention and will be apparent to those skilled in the art. For example, it may be desired to eliminate the use of thermoelectric module 50 and employ a longer cooling cycle. If thermoelectric module 50 is omitted, the period for which monostable multivibrator 148 develops a high state signal will be extended so that expansive element 34 can be cooled by normal conduction through heat conductors 58, fingers 56 and heat sink 52.

In an alternate embodiment, if it is not necessary to dissipate a great deal of heat, heat sink 52 can be eliminated. In a third embodiment, it may not be necessary or desirable for stopcock valve 24 to be rotated to three discrete positions. It is possible that stopcock valve 24 can be rotated to a first position for loading the sample and to a second position for heating element 34 and expelling the sample, then contracting expansive element 34. In this configuration cooling solenoid 78 can be omitted. Furthermore, because of heat losses through heat conductors 58 during the expansion of expansive element 34, it would be advantageous to employ the heating circuitry shown in U.S. patent application Ser. No. 584,142 now U.S. Pat. No. 3,973,196.

It should also be understood that other forms of and configurations of thermoelectric modules for cooling may be employed as well as other forms of particle ejecting device.

What is desired to be secured by Letters Patent in the United States is:

1. In a sample ejecting system including a sample ejecting device having means for receiving and temporarily storing an aliquot of sample including an inlet port and an outlet port connected in a first position, and a thermal expansion device mounted within said receiving and storing means operative to heat and expand into said storing means in a second position for ejecting a predetermined volume of said sample, the improvement comprising:
thermal conduction means coupled to said sample ejecting device, said thermal conduction means operative in a first mode following the ejection of said predetermined volume of said sample to conduct heat from said sample ejecting device for cooling and contracting said expansion device.

2. The sample ejecting device of claim 1 wherein said thermal conduction means include, a heat dissipation means for dissipating heat and thermal conduit means connecting said sample ejecting device and said heat dissipation means when said thermal conduction means is in said first mode for conducting heat from said sample ejecting device for cooling and contracting same.

3. The sample ejecting system of claim 2 wherein said heat dissipation means is a mechanical structure.

4. The sample ejecting system of claim 2 wherein said heat dissipation means is a thermoelectric device operative in said first mode to cool thermoelectrically for cooling and contracting said thermal expansion device.

5. The sample ejecting system of claim 4 further including control means coupled to said thermal conduit means and said thermal expansion device and operative to develop said first mode and at least a second mode, said control means being operative in said first mode to actuate said thermoelectric device to cool thermoelectrically for cooling and contracting said expansion device and operative in said second mode to couple a signal to said thermal expansion device for heating said device.

6. The sample ejecting system of claim 2 wherein said thermal expansion device includes an electric heating element, an expandable element surrounding said heating element having a given thermal coefficient of expansion, and an insulating jacket surrounding said expandable element, said thermal conduit means being coupled through said insulating jacket and contacting said expandable element for conducting heat therefrom.

7. The sample ejecting system of claim 6 wherein said thermal conduit means include a first portion secured to said expandable element and a second portion secured to said heat dissipation means, said first and second portions being coupled together when said thermal conduction means is in said first mode.

8. The sample ejecting system of claim 7 wherein at least one of said first and second portions is metallic.

9. The sample ejecting system of claim 7 wherein at least one of said first and second portions is nonmetallic.

10. The sample ejecting system of claim 7 further including control means coupled to said thermal conduit means and to said thermal expansion device and operative to develop said first mode and at least a second mode, said control means being operative in said first mode to couple together said first and second portions and operative in said second mode to uncouple said first and second portions and to couple a signal to said thermal expansion device for heating said device.

11. In a sample ejecting system including sample metering means having an accumulation chamber with an input port, an output port and an ejection port, shutoff means coupling said input port to a source of sample and said output port to a drain, said shutoff means operative in a first position to allow sample to pass through said accumulation chamber from said source to said drain, and operative in a second position to trap a volume of said sample within said accumulation chamber, said accumulation chamber having an ejecting means positioned therein including a thermal expansion device operative in response to a control signal to heat and expand into said chamber for ejecting a predetermined amount of said trapped sample, the improvement comprising:
thermal conduction means coupled to said ejecting means, said thermal conduction means operative in a first mode following the ejection of said predetermined amount of sample to conduct heat from said ejecting means for cooling and contracting same.

12. The system of claim 11 wherein said thermal conduction means include a heat dissipation means for dissipating heat and thermal conduit means connecting said ejecting means and said heat dissipation means when said thermal conduction means is in said first mode for conducting heat from said ejecting means for cooling and contracting same.

13. The sample ejecting system of claim 12 wherein said thermal expansion device includes an electric heating element, an expandable element surrounding said heating element and having a given thermal coefficient of expansion, and an insulating jacket surrounding said expandable element, said thermal conduit means being coupled through said insulating jacket and contacting said expandable element for conducting heat therefrom.

14. The sample ejecting system of claim 13 further including control means coupled to said shutoff means, said ejecting means and said thermal conduction means and operative to switch said shutoff means between said first and second positions, to develop said control signal when said shutoff means is in said second position, and to develop a first mode signal for operating said thermal conduction means in said first mode.

15. The sample ejecting system of claim 14 wherein said control means develops said first mode signal with said shutoff means positioned in said second position.

16. The sample ejecting system of claim 14 wherein said control means is further operative to switch said shutoff means to a third position, said control means being operative to develop said first mode signal with said shutoff means positioned in said third position.

17. The system of claim 14 wherein said sample metering means include a stopcock assembly having a stopcock valve rotatably mounted therein, said stopcock valve having said accumulation chamber formed therein and said input port, drain port and ejection port formed therein and in communication with said accumulation chamber, said assembly having said input and drain formed therein, said shutoff means including said stopcock valve, said stopcock valve being rotatable to said first position for aligning said input and input port and drain and drain port for receiving and expelling said sample, said stopcock valve being rotatable to said second position for blocking said input and drain port and trapping said volume of sample in said accumulation chamber.

18. The system of claim 17 wherein said thermal conduit means include a first portion mounted in said stopcock valve and coupled to said expandable element and a second portion secured to said stopcock assembly and communicating with said heat dissipation means.

19. The sample ejecting system of claim 18 wherein said control means develops said first mode signal with said shutoff means positioned in said second position and said first and second portions of said thermal conduit means are coupled together when said shutoff means is positioned in said second position.

20. The sample ejecting system of claim 18 wherein said heat dissipation means include thermoelectric means coupled to said second portion and to said control means and operative in response to said first mode signal developed therein to cool and increase the speed of heat dissipation.

21. The sample ejecting system of claim 18 wherein said heat dissipation means include a mechanical heat sink coupled to said second portion.

22. The sample ejecting system of claim 18 wherein said thermal conduit means first and second portions are in communication when said control means develops said first mode signal.

23. The sample ejecting system of claim 18 wherein said control means is further operative to switch said shutoff means to a third position, said thermal conduit means first and second portions being in communication when said shutoff means is in said third position, said control means being operative to develop said first mode signal with said shutoff means positioned in said third position.

24. The sample ejecting system of claim 20 wherein said first and second portions are in contact when said shutoff means is in said third position.

* * * * *